US011090428B2

(12) United States Patent
O'Neil et al.

(10) Patent No.: US 11,090,428 B2
(45) Date of Patent: Aug. 17, 2021

(54) SYRINGE INFUSION DEVICES AND SYSTEMS FOR DELIVERY OF ACTIVE AGENTS

(71) Applicant: PALMAYA PTY LTD., Subiaco (AU)

(72) Inventors: Alexander George Brian O'Neil, Subiaco (AU); Boon Yew Yeo, Subiaco (AU)

(73) Assignee: PALMAYA PTY LTD., Subiaco (AU)

( * ) Notice: Subject to any disclaimer, the term of this patent is extended or adjusted under 35 U.S.C. 154(b) by 0 days.

(21) Appl. No.: 15/511,690

(22) PCT Filed: Sep. 17, 2015

(86) PCT No.: PCT/AU2015/000572
§ 371 (c)(1),
(2) Date: Mar. 16, 2017

(87) PCT Pub. No.: WO2016/040990
PCT Pub. Date: Mar. 24, 2016

(65) Prior Publication Data
US 2017/0246381 A1 Aug. 31, 2017

(30) Foreign Application Priority Data

Sep. 17, 2014 (AU) ................................ 2014903710
Sep. 18, 2014 (AU) ................................ 2014903720

(51) Int. Cl.
*A61M 5/145* (2006.01)
*A61M 5/168* (2006.01)
(Continued)

(52) U.S. Cl.
CPC ........ *A61M 5/1454* (2013.01); *A61M 5/1456* (2013.01); *A61M 5/1458* (2013.01);
(Continued)

(58) Field of Classification Search
CPC ...... A61M 5/1454; A61M 2005/14506; A61M 5/14546
See application file for complete search history.

(56) References Cited

U.S. PATENT DOCUMENTS 4,202,333 A   5/1980 Strand et al.
4,381,006 A * 4/1983 Genese ............... A61M 5/1454
                                                128/DIG. 12
(Continued)

OTHER PUBLICATIONS

Search Report—Corresponding PCT Application No. PCT/AU2015/000572, dated Nov. 27, 2015, 7 pages.
(Continued)

*Primary Examiner* — Emily L Schmidt
(74) *Attorney, Agent, or Firm* — Leber IP Law; Shelly M. Fujikawa

(57) ABSTRACT

A pump device (10) operable with a syringe (11) having a barrel (12) and a plunger (13). The pump device (10) is operable to cause relative movement between the syringe plunger (13) and the syringe barrel (12) for discharging fluid from the syringe (11). The pump device (10) comprises a portion (31) adapted to engage the syringe barrel (12), and a drive mechanism for moving the syringe plunger (13) relative to the syringe barrel (12) to discharge fluid from the syringe (11). The drive mechanism comprises an actuator (45) adapted to engage the syringe plunger (13) and a power mechanism (61) for moving the actuator (45) to effect movement of the syringe plunger (13) relative to the syringe barrel (12). The pump device (10) thus provides a syringe driving means. There is also provided an infusion system comprising a syringe driving means, the syringe driving means comprising the pump device (10). Further, there is provided an infusion system comprising a syringe driving means operable to maintain a constant pressure within a syringe and tubing with viscosity corrections for various antibiotic concentrations.

13 Claims, 11 Drawing Sheets

(51) Int. Cl.
*A61M 5/142* (2006.01)
*A61M 5/14* (2006.01)

(52) U.S. Cl.
CPC .... *A61M 5/14546* (2013.01); *A61M 5/16813* (2013.01); *A61M 5/16881* (2013.01); *A61M 5/141* (2013.01); *A61M 5/14244* (2013.01); *A61M 2005/1405* (2013.01); *A61M 2205/70* (2013.01); *A61M 2205/7536* (2013.01); *A61M 2209/088* (2013.01)

(56) References Cited

U.S. PATENT DOCUMENTS

| | | |
|---|---|---|
| 4,755,172 A | 7/1988 | Baldwin |
| 4,863,429 A | 9/1989 | Baldwin |
| 7,270,648 B2 | 9/2007 | Kazemzadeh |
| 7,867,197 B2 | 1/2011 | Sims et al. |
| 2004/0122366 A1 | 6/2004 | Kazemzadeh |
| 2004/0152979 A1* | 8/2004 | Sakakibara ......... A61M 5/1458 600/432 |
| 2005/0033233 A1* | 2/2005 | Kriesel ............... A61M 5/1454 604/133 |
| 2006/0186143 A1* | 8/2006 | Argentine ........... A61M 5/1454 222/336 |
| 2011/0028897 A1* | 2/2011 | Swan ................. A61M 5/1454 604/151 |
| 2013/0053790 A1* | 2/2013 | Karlsson ............ A61M 5/2033 604/218 |

OTHER PUBLICATIONS

Supplemental European Search Report—European Application No. 15842037.2, dated May 25, 2018, 7 pages.

* cited by examiner

| Measured FCT Flow Rate | | |
|---|---|---|
| Length | 500 | mm |
| Diameter | 14 | thou |
| Flow Rate | 3.27 | ml/min |

| FCT to be calibrated | | |
|---|---|---|
| Infusion volume | 60 | ml |

Length of FCT to be calibrated at different flow rates (mm)

| Infusion Time | | FCT Diameter (thou) | | | | | | | | | | | |
|---|---|---|---|---|---|---|---|---|---|---|---|---|---|
| in hr | in min | 3 | 4 | 5 | 6 | 7 | 8 | 9 | 10 | 11 | 12 | 13 | 14 | 15 |
|  | 5 | 0.3 | 0.9 | 2.2 | 4.6 | 8.5 | 14.5 | 23.3 | 35.5 | 51.9 | 73.5 | 101.3 | 136.3 | 179.6 |
|  | 15 | 0.9 | 2.7 | 6.7 | 13.8 | 25.5 | 43.6 | 69.8 | 106.4 | 155.8 | 220.6 | 303.9 | 408.8 | 538.7 |
|  | 30 | 1.7 | 5.4 | 13.3 | 27.6 | 51.1 | 87.2 | 139.6 | 212.8 | 311.6 | 441.3 | 607.8 | 817.5 | 1077.3 |
|  | 60 | 3.4 | 10.9 | 26.6 | 55.2 | 102.2 | 174.3 | 279.2 | 425.6 | 623.1 | 882.5 | 1215.6 | 1635.0 | 2154.6 |
| 2 |  | 6.9 | 21.8 | 53.2 | 110.3 | 204.4 | 348.7 | 558.5 | 851.2 | 1246.3 | 1765.1 | 2431.1 | 3270.0 | 4309.2 |
| 4 |  | 13.8 | 43.6 | 106.4 | 220.6 | 408.8 | 697.3 | 1117.0 | 1702.4 | 2492.5 | 3530.1 | 4862.3 | 6540.0 | 8618.5 |
| 6 |  | 20.7 | 65.4 | 159.6 | 330.9 | 613.1 | 1046.0 | 1675.4 | 2553.6 | 3738.8 | 5295.2 | 7293.4 | 9810.0 | 12927.7 |
| 8 |  | 27.6 | 87.2 | 212.8 | 441.3 | 817.5 | 1394.6 | 2233.9 | 3404.8 | 4985.0 | 7060.3 | 9724.5 | 13080.0 | 17237.0 |
| 12 |  | 41.4 | 130.7 | 319.2 | 661.9 | 1226.3 | 2091.9 | 3350.9 | 5107.2 | 7477.5 | 10590.4 | 14586.8 | 19620.0 | 25855.4 |
| 24 |  | 82.7 | 261.5 | 638.4 | 1323.8 | 2452.5 | 4183.9 | 6701.7 | 10214.5 | 14955.0 | 21180.8 | 29173.6 | 39240.0 | 51710.9 |
| 48 |  | 165.5 | 523.0 | 1276.8 | 2647.6 | 4905.0 | 8367.7 | 13403.5 | 20429.0 | 29910.1 | 42361.5 | 58347.2 | 78480.0 | 103421.8 |
| 72 |  | 248.2 | 784.5 | 1915.2 | 3971.4 | 7357.5 | 12551.6 | 20105.2 | 30643.5 | 44865.1 | 63542.3 | 87520.8 | 117720.0 | 155132.6 |
| 96 |  | 330.9 | 1046.0 | 2553.6 | 5295.2 | 9810.0 | 16735.4 | 26806.9 | 40858.0 | 59820.2 | 84723.1 | 116694.5 | 156960.0 | 206843.5 |

Length of FCT to be calibrated at different flow rates (mm)

| Infusion Time | | FCT Diameter (thou) | | | | | | | | | | | |
|---|---|---|---|---|---|---|---|---|---|---|---|---|---|
| in hr | in min | 16 | 17 | 18 | 19 | 20 | 21 | 22 | 23 | 24 | 25 | 26 | 27 | 28 |
|  | 5 | 232.4 | 296.2 | 372.3 | 462.2 | 567.5 | 689.8 | 830.8 | 992.5 | 1176.7 | 1385.4 | 1620.8 | 1884.9 | 2180.0 |
|  | 15 | 697.3 | 888.7 | 1117.0 | 1386.6 | 1702.4 | 2069.3 | 2492.5 | 2977.5 | 3530.1 | 4156.3 | 4862.3 | 5654.6 | 6540.0 |
|  | 30 | 1394.6 | 1777.3 | 2233.9 | 2773.3 | 3404.8 | 4138.6 | 4985.0 | 5955.1 | 7060.3 | 8312.6 | 9724.5 | 11309.2 | 13080.0 |
|  | 60 | 2789.2 | 3554.7 | 4467.8 | 5546.5 | 6809.7 | 8277.2 | 9970.0 | 11910.1 | 14120.5 | 16652.2 | 19449.1 | 22618.3 | 26160.0 |

Fig. 12

Measured FCT Flow Rate

| | | |
|---|---|---|
| Length | 500 | mm |
| Diameter | 14 | thou |
| Flow Rate | 3.27 | ml/min |

FCT to be calibrated

| | | |
|---|---|---|
| Infusion volume | 60 | ml |

Length of FCT to be calibrated at different flow rates (mm)

| Infusion Time | | FCT Diameter (thou) | | | | | | | | | | | |
|---|---|---|---|---|---|---|---|---|---|---|---|---|---|
| in hr | in min | 3 | 4 | 5 | 6 | 7 | 8 | 9 | 10 | 11 | 12 | 13 | 14 | 15 |
| | 60 | 3.4 | 10.9 | 26.6 | 55.2 | 102.2 | 174.3 | 279.2 | 425.6 | 623.1 | 882.5 | 1218.6 | 1635.0 | 2154.6 |
| 13 | 780 | 44.8 | 141.6 | 345.8 | 717.1 | 1328.4 | 2265.3 | 3630.1 | 5532.9 | 8100.6 | 11472.9 | 15802.4 | 21255.0 | 28010.1 |
| 19 | 1140 | 65.5 | 207.0 | 505.4 | 1048.0 | 1941.6 | 3312.2 | 5305.5 | 8086.5 | 11839.4 | 16768.1 | 23095.8 | 31065.0 | 40937.8 |

Fig. 13

For 60 ml

| Infusion Time | | \multicolumn{13}{c|}{Length of FCT to be calibrated at different flow rates (mm)} |
| | | \multicolumn{13}{c|}{FCT Diameter (thou)} |
| in hr | in min | 3 | 4 | 5 | 6 | 7 | 8 | 9 | 10 | 11 | 12 | 13 | 14 | 15 |
|---|---|---|---|---|---|---|---|---|---|---|---|---|---|---|
| | 5 | 0.3 | 0.9 | 2.2 | 4.6 | 8.5 | 14.5 | 23.3 | 35.5 | 51.9 | 73.5 | 101.3 | 136.3 | 179.6 |
| | 15 | 0.9 | 2.7 | 6.7 | 13.8 | 25.5 | 43.6 | 69.8 | 106.4 | 155.8 | 220.6 | 303.9 | 408.8 | 538.7 |
| | 30 | 1.7 | 5.4 | 13.3 | 27.6 | 51.1 | 87.2 | 139.6 | 212.8 | 311.6 | 441.3 | 607.8 | 817.5 | 1077.3 |
| | 60 | 3.4 | 10.9 | 26.6 | 55.2 | 102.2 | 174.3 | 279.2 | 425.6 | 623.1 | 882.5 | 1215.6 | 1635.0 | 2154.6 |
| 2 | 120 | 6.9 | 21.8 | 53.2 | 110.3 | 204.4 | 348.7 | 558.5 | 851.2 | 1246.3 | 1765.1 | 2431.1 | 3270.0 | 4309.2 |
| 4 | 240 | 13.8 | 43.6 | 106.4 | 220.6 | 408.8 | 697.3 | 1117.0 | 1702.4 | 2492.5 | 3530.1 | 4862.3 | 6540.0 | 8618.5 |
| 6 | 360 | 20.7 | 65.4 | 159.6 | 330.9 | 613.1 | 1046.0 | 1675.4 | 2553.6 | 3738.8 | 5295.2 | 7293.4 | 9810.0 | 12927.7 |
| 8 | 480 | 27.6 | 87.2 | 212.8 | 441.3 | 817.5 | 1394.6 | 2233.9 | 3404.8 | 4985.0 | 7060.3 | 9724.5 | 13080.0 | 17237.0 |
| 12 | 720 | 41.4 | 130.7 | 319.2 | 661.9 | 1226.3 | 2091.9 | 3350.9 | 5107.2 | 7477.5 | 10590.4 | 14586.8 | 19620.0 | 25855.4 |
| 13 | 780 | 44.8 | 141.6 | 345.8 | 717.1 | 1328.4 | 2266.3 | 3630.1 | 5532.9 | 8100.6 | 11472.9 | 15802.4 | 21255.0 | 28010.1 |
| 19 | 1140 | 65.5 | 207.0 | 505.4 | 1048.0 | 1941.6 | 3312.2 | 5305.5 | 8086.5 | 11839.4 | 16768.1 | 23095.8 | 31065.0 | 40937.8 |
| 24 | 1440 | 82.7 | 261.5 | 638.4 | 1323.8 | 2452.5 | 4183.9 | 6701.7 | 10214.5 | 14955.0 | 21180.8 | 29173.6 | 39240.0 | 51710.9 |
| 48 | 2880 | 165.5 | 523.0 | 1276.8 | 2647.6 | 4905.0 | 8367.7 | 13403.5 | 20429.0 | 29910.1 | 42361.5 | 58347.2 | 78480.0 | 103421.8 |
| 72 | 4320 | 248.2 | 784.5 | 1915.2 | 3971.4 | 7357.5 | 12551.6 | 20105.2 | 30643.5 | 44865.1 | 63542.3 | 87520.8 | 117720.0 | 155132.6 |
| 96 | 5760 | 330.9 | 1046.0 | 2553.6 | 5295.2 | 9810.0 | 16735.4 | 26806.9 | 40858.0 | 59820.2 | 84723.1 | 116694.5 | 156960.0 | 206843.5 |

Fig. 14

For 100 ml

| Infusion Time | | Length of FCT to be calibrated at different flow rates (mm) | | | | | | | | | | | | |
|---|---|---|---|---|---|---|---|---|---|---|---|---|---|---|
| | | FCT Diameter (thou) | | | | | | | | | | | | |
| in hr | in min | 3 | 4 | 5 | 6 | 7 | 8 | 9 | 10 | 11 | 12 | 13 | 14 | 15 |
| | 5 | 0.2 | 0.5 | 1.3 | 2.8 | 5.1 | 8.7 | 14.0 | 21.3 | 31.2 | 44.1 | 60.8 | 81.8 | 107.7 |
| | 15 | 0.5 | 1.6 | 4.0 | 8.3 | 15.3 | 26.1 | 41.9 | 63.8 | 93.5 | 132.4 | 182.3 | 245.3 | 323.2 |
| | 30 | 1.0 | 3.3 | 8.0 | 16.6 | 30.7 | 52.3 | 83.8 | 127.7 | 186.9 | 264.8 | 364.7 | 490.5 | 646.4 |
| | 60 | 2.1 | 6.5 | 16.0 | 33.1 | 61.8 | 104.6 | 167.5 | 255.4 | 373.9 | 529.5 | 729.3 | 981.0 | 1292.8 |
| 2 | 120 | 4.1 | 13.1 | 31.9 | 66.2 | 122.6 | 209.2 | 335.1 | 510.7 | 747.8 | 1059.0 | 1458.7 | 1962.0 | 2585.5 |
| 4 | 240 | 8.3 | 26.1 | 63.8 | 132.4 | 245.3 | 418.4 | 670.2 | 1021.4 | 1495.5 | 2118.1 | 2917.4 | 3924.0 | 5171.1 |
| 6 | 360 | 12.4 | 39.2 | 95.8 | 198.6 | 367.9 | 627.6 | 1005.3 | 1532.2 | 2243.3 | 3177.1 | 4376.0 | 5886.0 | 7756.6 |
| 8 | 480 | 16.5 | 52.3 | 127.7 | 264.8 | 490.5 | 836.8 | 1340.3 | 2042.9 | 2991.0 | 4236.2 | 5834.7 | 7848.0 | 10342.2 |
| 12 | 720 | 24.8 | 78.4 | 191.5 | 397.1 | 735.8 | 1255.2 | 2010.5 | 3064.3 | 4486.5 | 6354.2 | 8752.1 | 11772.0 | 15513.3 |
| 13 | 780 | 26.9 | 85.0 | 207.5 | 430.2 | 797.1 | 1359.8 | 2178.1 | 3319.7 | 4860.4 | 6883.8 | 9481.4 | 12753.0 | 16806.0 |
| 19 | 1140 | 39.3 | 124.2 | 303.2 | 628.8 | 1164.9 | 1987.3 | 3183.3 | 4851.9 | 7103.6 | 10060.9 | 13857.5 | 18639.0 | 24562.7 |
| 24 | 1440 | 49.6 | 156.9 | 383.0 | 794.3 | 1471.5 | 2510.3 | 4021.0 | 6128.7 | 8973.0 | 12708.5 | 17504.2 | 23544.0 | 31026.7 |
| 48 | 2880 | 99.3 | 313.8 | 766.1 | 1588.6 | 2943.0 | 5020.6 | 8042.1 | 12257.4 | 17946.0 | 25416.9 | 35008.3 | 47088.0 | 62053.1 |
| 72 | 4320 | 148.9 | 470.7 | 1149.1 | 2382.8 | 4414.5 | 7530.9 | 12063.1 | 18386.1 | 26919.1 | 38125.4 | 52512.5 | 70632.0 | 93079.6 |
| 96 | 5760 | 198.6 | 627.6 | 1532.2 | 3177.1 | 5886.0 | 10041.3 | 16084.2 | 24514.8 | 35892.1 | 50833.9 | 70016.7 | 94176.0 | 1241061 |

Fig. 15

SYRINGE INFUSION DEVICES AND SYSTEMS FOR DELIVERY OF ACTIVE AGENTS

TECHNICAL FIELD

The invention relates generally to the field of devices for administering a substance via a syringe.

The invention has been devised particularly, although not necessarily solely, in relation to administration of a therapeutic substance via a syringe. Accordingly, the following discussion in relation to background art is provided in the context of collection of administration of therapeutic substances. However, the invention may have application in various other fields involving administration of substances via syringe.

BACKGROUND ART

The following discussion of the background art is intended to facilitate an understanding of the present invention only. The discussion is not an acknowledgement or admission that any of the material referred to is or was part of the common general knowledge as at the priority date of the application.

In very general terms, a syringe is a hand-held device comprising a barrel and a plunger, which may be operated manually by a person applying pressure to the plunger, forcing the contents, usually a substance, such as a fluid, from the barrel to the outside via an outlet in the barrel. In use, the outlet may be connected directly to a needle, tubing or cannula.

The fluid contained within the syringe may be administered to a patient at a pre-determined rate over a pre-determined period of time to ensure the safe and therapeutic delivery of an active agent contained within the fluid. This is not possible with a handheld syringe. Thus, a system that delivers a constant amount of the fluid at a constant rate is required. In addition, it is also desirable to have a system that allows for the administration of the active agent to be administered within a hospital setting or at home. Therefore, the pump infusion system would preferably be portable.

Known pump systems for use with syringes do not necessarily apply a constant pressure to the plunger, therefore resulting in an uneven flow rate of the substance from the syringe. In addition, the administration of a substance using known cannula or tubing systems may not necessarily result in the accurate administration of a substance, such as a therapeutic substance.

It is therefore an aim of the present invention to provide systems that can be used with a syringe that results in at least a constant flow rate of a substance.

SUMMARY OF INVENTION

In one aspect of the present invention, there is provided a pump device operable with a syringe having a barrel and a plunger, the pump device being operable to cause relative movement between the syringe plunger and the syringe barrel for discharging fluid from the syringe, the pump device comprising a portion adapted to engage the syringe barrel, and a drive mechanism for moving the syringe plunger relative to the syringe barrel to discharge fluid from the syringe, the drive mechanism comprising an actuator adapted to engage the syringe plunger and a power mechanism for moving the actuator to effect movement of the syringe plunger relative to the syringe barrel.

The power mechanism may have a first condition which it assumes when not in operation and a second condition from which it is operable to move the syringe plunger relative to the barrel.

The power mechanism may be adapted to be energising upon movement from the first condition to the second condition.

Preferably, the power mechanism is movable from the first condition to the second condition upon installation of the syringe on the syringe pump.

The actuator may comprise a piston movable along a path.

The piston may be adapted for guided movement along the path.

The power mechanism may comprise at least one spring mechanism operable to exert a spring force on the actuator.

Preferably, the power mechanism comprises two spring mechanisms.

The two spring mechanisms may be disposed on opposed sides of the path along which actuator is movable. This arrangement facilitates the application of a relatively even or uniform force on opposed sides of the syringe plunger.

The spring mechanism, or each of the spring mechanisms, may comprise a reel, a spring adapted to be tensioned upon winding of the reel in one direction, and a flexible link extending between the reel and the actuator, the flexible link being windable onto and from the reel, the reel being wound in said one direction to cause tensioning of the spring upon winding of the flexible link from the reel, whereby the tensioned spring biases the reel to cause rotation thereof in the opposite direction.

With this arrangement, the spring mechanism can be loaded by displacement of the actuator against the biasing action of the spring force upon installation of the syringe on the syringe on the syringe pump.

The spring may comprise a spring of the type known as a constant force spring. Such a spring delivers a constant spring force when under load. Any appropriate spring that is known in the art may be used. Preferably, the spring comprises a spring capable of delivering a substantially uniform spring force when in a loaded condition; for example, a spring of known kind of the type commonly referred to as a watch spring.

Where there are two spring mechanisms disposed on opposed sides of the path along which actuator is movable, the two flexible links may be coupled to a base portion of the actuator.

Further, the two springs may be of identical size and loaded at an identical pressure. The springs when loaded may deliver a constant force of about 25 N each.

The use and position of the springs allow for the piston to keep the axial centre line of the syringe constant, thereby allowing for a constant delivery of the fluid from the syringe. In other words, the symmetrical arrangement of the two springs with the piston minimises the friction between the piston and the internal wall of the body of the pump device.

The portion of the pump device adapted to engage the syringe barrel may comprise an engaging means for releasably engaging an end section of the barrel from which the plunger extends.

The engaging means may comprise a receptor in which the end section of the barrel is releasably received.

The receptor may be configured as a socket formation for operation in conjunction with the end section of the barrel to provide a connection therebetween.

The socket formation may be configured to provide a bayonet connection.

The end section of the barrel is typically provided with a lateral protrusion configured for engagement by the fingers of a user of the syringe. The lateral protrusion typically comprises two opposed lugs against which the user can locate fingers of a hand in which the syringe is being held to restrain the syringe barrel while pushing the syringe plunger with the thumb of that hand. With this arrangement, the two opposed lugs may function as two bayonet pins for engagement with counterpart bayonet slots provided in the receptor.

The syringe pump may further comprise a body defining a cavity in which the actuator is accommodated, the cavity defining the path along which the actuator is movable, the receptor being provided adjacent one end of the cavity whereby the syringe plunger is receivable in the cavity for engagement with the actuator when the end section of the barrel is received in the receptor.

The cavity may comprise a passage configured to define a barrel portion along which the actuator is guidingly movable. That is, the barrel portion of the passage is configured to accommodate guided movement of the actuator along the passage.

When the actuator is in a condition remote from the receptor, the cavity may be of a size to accommodate the length of the syringe plunger when the latter is fully withdrawn from the syringe barrel.

The pump device may further comprise one or more attachments points. The attachment point(s) may comprise hook(s) positioned on the body to allow for a lanyard or strap to be threaded therethrough. The hook(s) allow for the pump device to be hung around the neck of a patient or on a stand.

In another aspect of the present invention, there is provided a pump device operable with a syringe having a syringe barrel and a syringe plunger, the pump device being operable to cause relative movement between the syringe plunger and the syringe barrel for discharging fluid from the syringe, the pump device comprising a portion adapted to engage the syringe barrel, and a drive mechanism for moving the syringe plunger relative to the barrel to discharge fluid from the syringe, said portion adapted to engage the syringe barrel comprising a receptor configured for operation in conjunction with an end section of the syringe barrel to provide a releasable connection therebetween.

Preferably, the releasable connection comprises a bayonet connection.

In one embodiment of the present invention the springs are of identical size and loaded at an identical pressure. The springs when loaded may deliver a constant force of about 25 N each.

Any appropriate spring may be used that is known in the art. Preferably, the spring comprises a spring capable of delivering a substantially uniform spring force when in a loaded condition; for example, a spring of known kind of the type commonly referred to as a watch spring.

The use and position of the springs allow for the piston to keep the axial centre line of the syringe constant, thereby allowing for a constant delivery of the fluid from the syringe. In other words, the symmetrical arrangement of the two springs with the piston minimises the friction between the piston and the internal wall of the body of the pump device.

In a further aspect, the present invention provides an infusion system comprising a syringe driving means, the syringe driving means comprising a pump device according to any one of the aspects of the invention as set forth above.

In a further aspect, the present invention provides an infusion system comprising a syringe driving means operable to maintain a constant pressure within a syringe, (and tubing with viscosity corrections for various antibiotic concentrations.

The tubing may be calibrated to restrict the flow of fluid thereby delivering a selected profile of antibiotic. The selected profile may comprise the ideal profile of antibiotic to maximise the concentration of antibiotic above the mean inhibitory concentration (MIC) of the antibiotic to a patient in need thereof. The desirable flow rate may also protect the integrity of the veins. The infusion system of the present invention may be used in the hospital setting or in the home environment for peripheral line, peripheral inserted central catheter (PICC) or central line antibiotic delivery.

In a further aspect, the present invention provides an infusion system comprising tubing with viscosity corrections for various antibiotic concentrations. The tubing may be calibrated to restrict the flow of fluid thereby delivering the ideal profile of antibiotic to maximise the concentration of antibiotic above the mean inhibitory concentration (MIC) of the antibiotic to a patient in need thereof. The desirable flow rate also protects the integrity of the veins. The infusion system of the present invention may be used in the hospital setting or in the home environment for peripheral line, peripheral inserted central catheter (PICC) or central line antibiotic delivery.

In another aspect, the present invention provides a kit comprising a syringe, a syringe driving means and tubing calibrated for delivering a pre-determined amount of an antibiotic in a pre-determined time period. A kit comprising a tubing calibrated for use with an antibiotic solution is also provided by the present invention.

The syringe driving means forming part of the kit may comprise a pump device. The pump device may comprise a pump device according to any one of the aspects of the invention as set forth above.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 12 are Flow Control Tubing Charts for an infusion volume of 60 ml;

FIG. 13 is the Flow Control Tubing Chart for an infusion volume of 60 ml at 13 and 19 hours;

FIG. 14 is the Flow Control Tubing Chart for an infusion volume of 60 ml from 5 minutes to 96 hours; and FIG. 15 is the Flow Control Tubing Chart for an infusion volume of 100 ml from 5 minutes to 96 hours.

Figure 1:
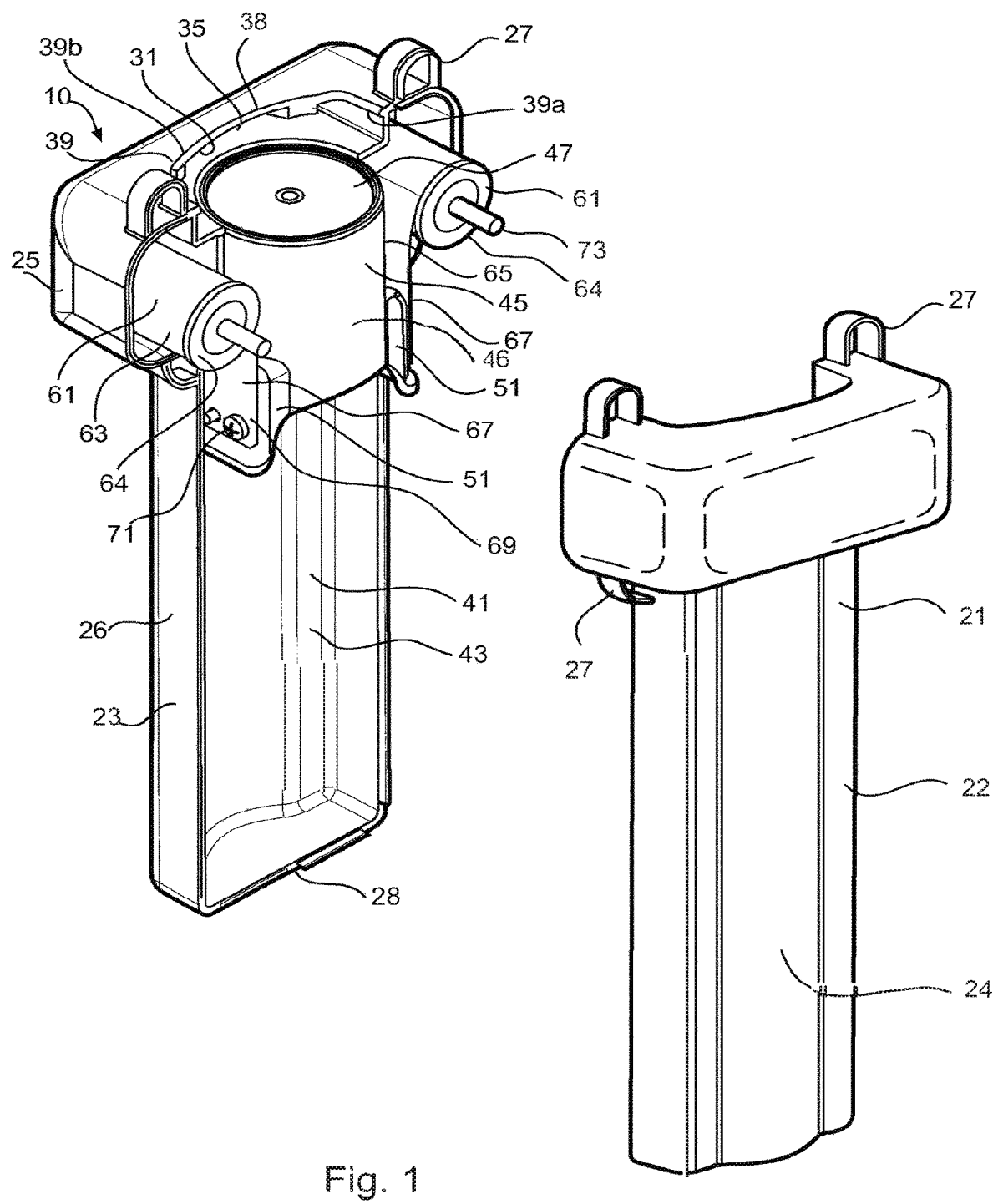
FIG. 1 is an exploded perspective view of a first embodiment of a syringe pump according to the invention.
Figure 2:
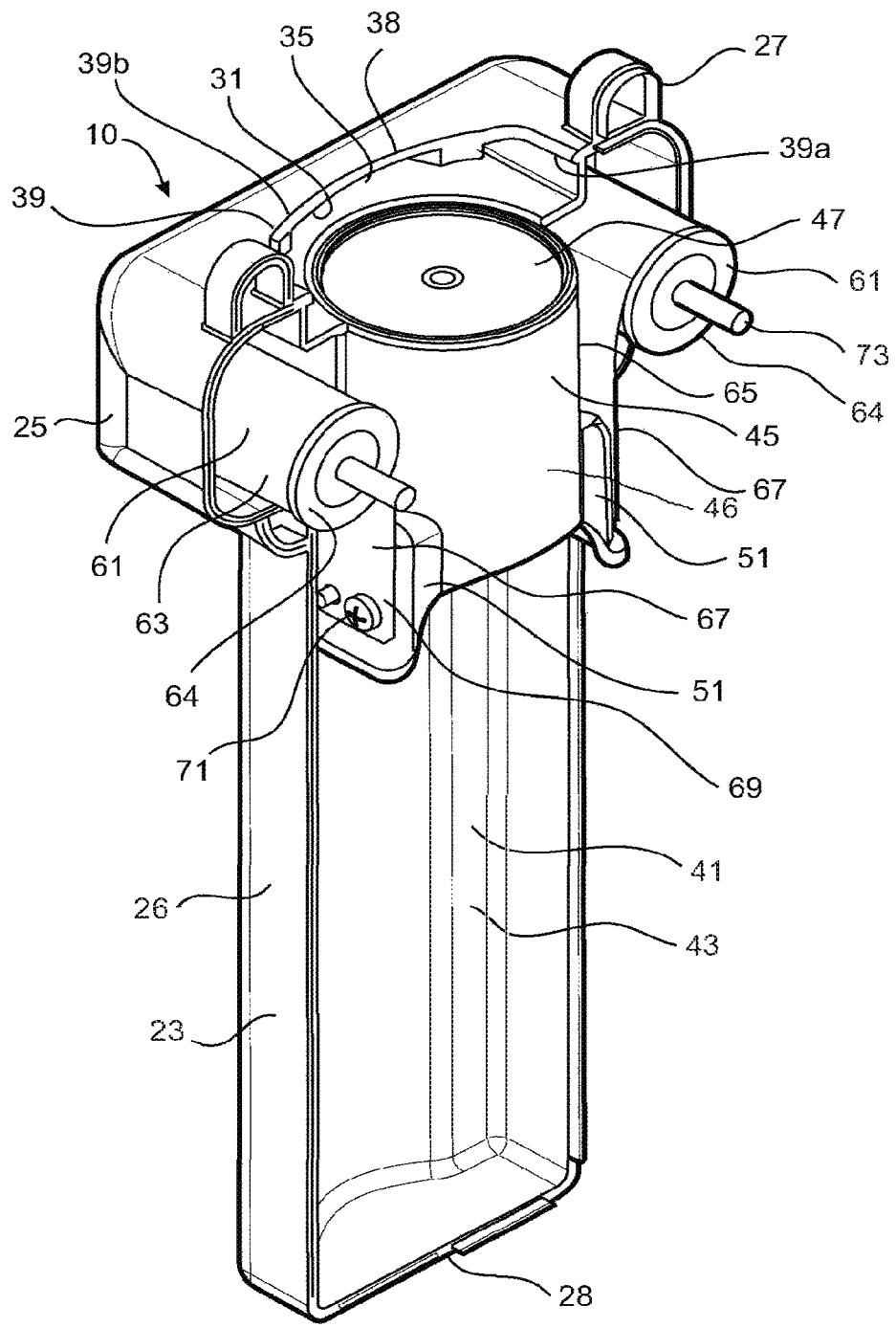
FIG. 2 is a perspective view of part of the arrangement shown in FIG. 1.
Figure 3:
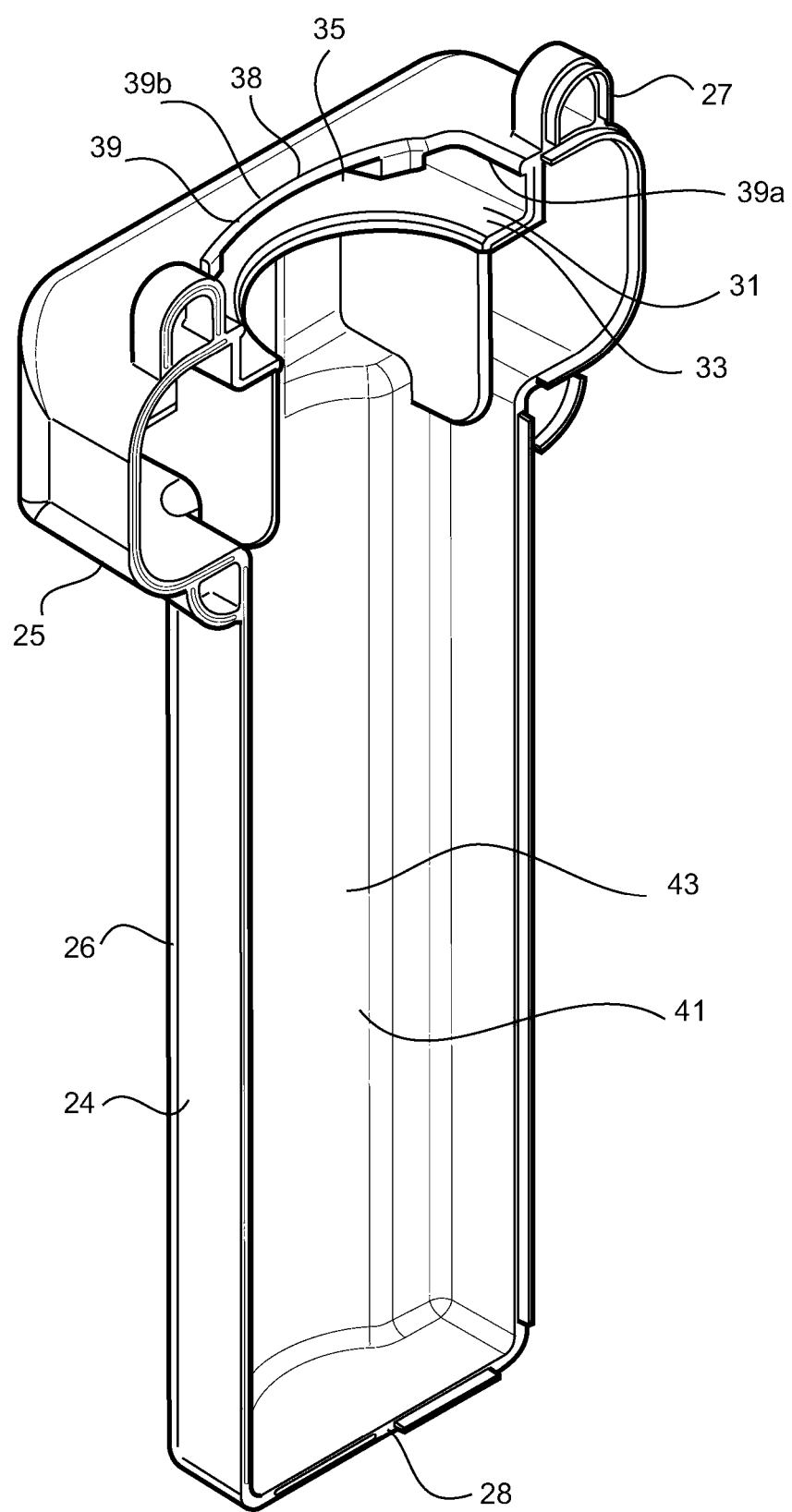
FIG. 3 is a perspective view of another part of the arrangement shown in FIG. 1.
Figure 4:
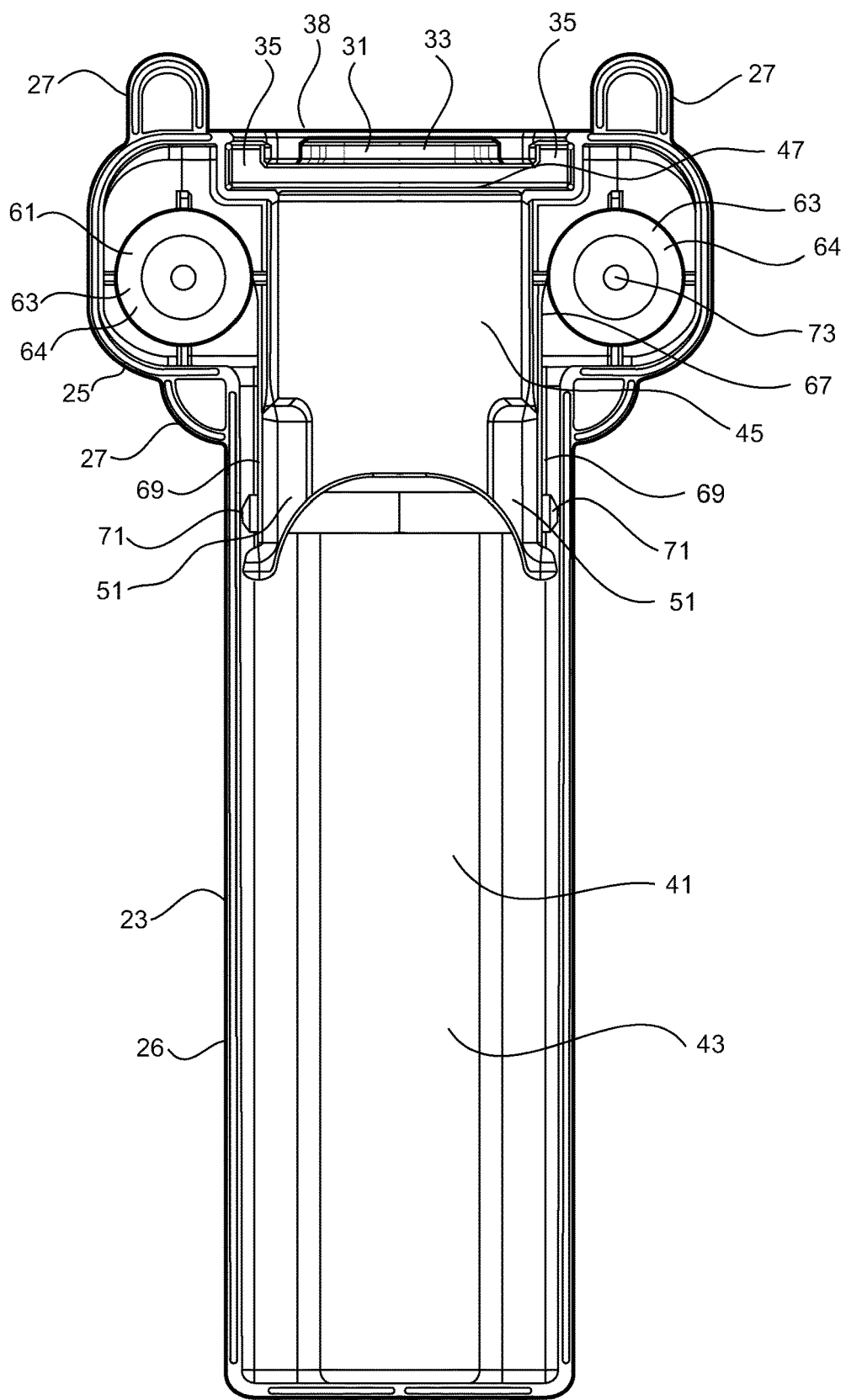
FIG. 4 is an elevational view of the part shown in FIG. 2.
Figure 5:
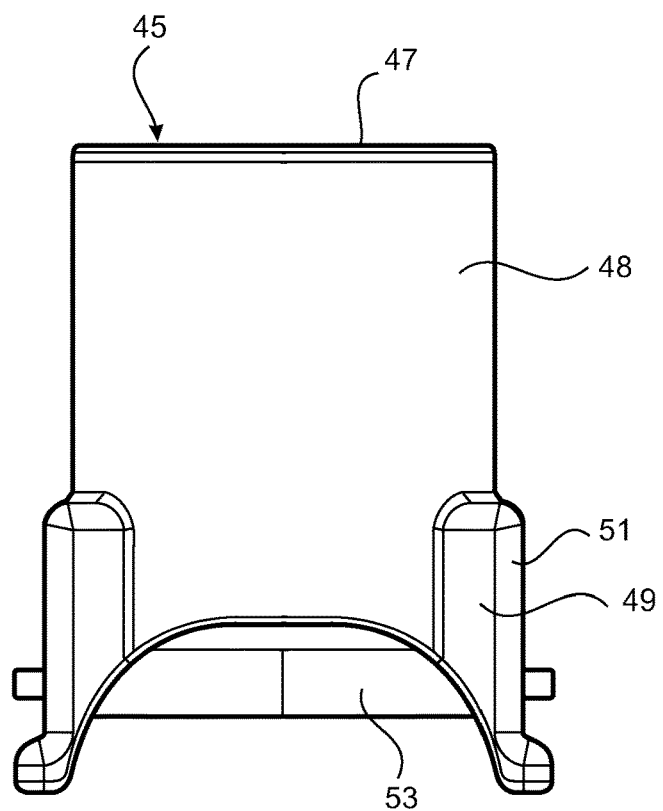
FIG. 5 is a side view of an actuator forming part of the syringe pump.
Figure 6:
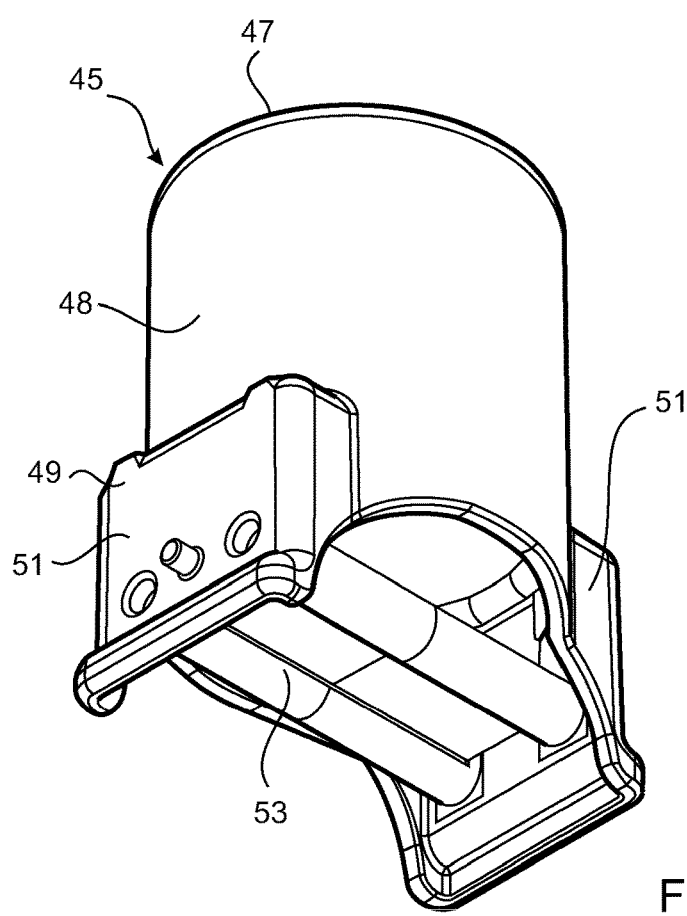
FIG. 6 is a perspective view of the actuator.

In the drawings like structures are referred to by like numerals throughout the several views. The drawings shown are not necessarily to scale, with emphasis instead generally being placed upon illustrating the principles of the present invention The figures depict an embodiment of the invention. The embodiment illustrates certain configurations; however, it is to be appreciated that the invention can take the form of many configurations, as would be obvious to a person skilled in the art, whilst still embodying the present invention. These configurations are to be considered within the scope of this invention.

DESCRIPTION OF EMBODIMENTS

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, displacement and field strength etc.). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active.

Reference to positional descriptions, such as "upper", "lower", "top" and "bottom", are to be taken in context of the embodiments depicted in the drawings, and are not to be taken as limiting the invention to the literal interpretation of the term but rather as would be understood by the skilled addressee.

Additionally, where the terms "system", "device", and "apparatus" are used in the context of the invention, they are to be understood as including reference to any group of functionally related or interacting, interrelated, interdependent or associated components or elements that may be located in proximity to, separate from, integrated with, or discrete from, each other.

Throughout this specification, unless the context requires otherwise, the word "comprise" or variations such as "comprises" or "comprising", will be understood to imply the inclusion of a stated integer or group of integers but not the exclusion of any other integer or group of integers.

DETAILED DESCRIPTION OF THE INVENTION

The present invention provides a device which allows a constant flow of a fluid from a syringe. Due to the arrangement of the syringe within known infusion systems, it is often not possible to routinely obtain a constant flow rate, since the centre line of the syringe with respect to the pushing force created by the plunger is uneven, leading to inaccuracies in the flow rate.

The device of the present invention seeks to address this problem by providing an even force to each side of the flange of the plunger.

Referring to FIGS. 1 to 6, there is shown a first embodiment of a syringe infusion device according to the invention comprising a syringe driving means in the form of a pump device 10. The pump device 10 will hereinafter be referred to as a syringe pump.

The syringe pump 10 is operable with a syringe 11 of known kind, the syringe 11 having a syringe barrel 12 and a syringe plunger 13 moveable relative to the syringe barrel for discharging fluid from the syringe through discharge outlet 14 at the front end of the syringe. The rear end section 12a of the syringe barrel 12 is provided with a lateral protrusion 15 configured for engagement by the fingers of a user of the syringe. The lateral protrusion 15 comprises two opposed lugs 16 against which the user can locate fingers of a hand in which the syringe is being held to restrain the syringe barrel while pushing the syringe plunger 13 with the thumb of that hand. The rear end section of the syringe plunger 13 is provided with a formation 18 which functions as a button to receive the thumb of the user.

The syringe pump 10 comprises a body 21 defining a housing 22 comprising two housing sections 23, 24 adapted to the fitted together. The two housing sections 23, 24 are shown in a separated condition in FIG. 1 to reveal the internal workings of the syringe pump 10.

The body 21 comprises an upper section 25 and a lower section 26. The upper section 25 incorporates attachment points 27, such as for example lugs, by means of which the syringe pump 10 may be attached to support apparatus or suspended from, for example, a lanyard worn by a patient. The lower section 26 has a base portion 28 configured to rest on a supporting surface such as a table.

Figure 7:
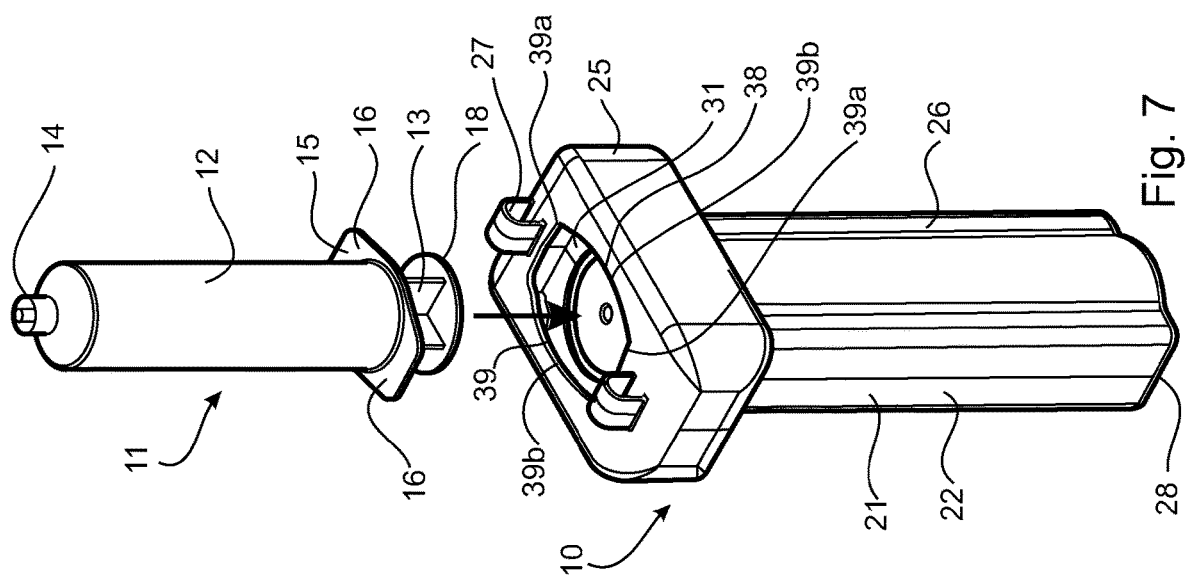
FIG. 7 is a perspective view showing a syringe being presented to the syringe pump for installation thereon.

The upper section 25 comprises a receptor 31 by means of which syringe 11 may be mounted onto the syringe pump 10. The receptor 31 is configured as a socket formation 33 having slots 35 operable in conjunction with the two opposed lugs 16 of the syringe 11 to provide a bayonet connection 37 therebetween. Specifically, the socket formation 33 has an entry end 38 configured to receive the lateral protrusion 15 on the rear end section of the syringe barrel 12 when the syringe barrel is in one orientation (as depicted in FIG. 7) and into restrain the lateral protrusion 15 against withdrawal through the entry end 38 when the syringe barrel is rotated out of that particular orientation (as shown in FIG.

8). In the arrangement shown, the entry end 38 is configured to define a periphery 39 have two opposed end sections 39a and two further opposed end sections 39b. The two opposed end section 39a facilitate entry of the end section of the syringe barrel 12 when the two opposed lugs 16 are in registration with the end sections 39a. Further, the slots 35 are provided adjacent two opposed end section 39b to preclude withdrawal of the lateral protrusion 15 from the socket formation 33 through the entry end 38 when the syringe barrel 12 is in an orientation in which the lugs 16 are out of registration with the end sections 39a.

The body 21 defines a cavity 41 in the form of a passage 43 which opens at one end onto the socket formation 33 and which extends downwardly to adjacent the base 27 at the other end.

An actuator 45 is accommodated within the passage 43 for movement towards and away from the socket formation 33. In the arrangement shown, the actuator 45 comprises a piston 46 having an upper end face 47 which defines a platform for engaging the formation 18 at the end of the syringe plunger 13 and driving the syringe plunger inwardly with respect to the syringe barrel 12 to discharge fluid from the syringe 11 through the discharge outlet 14.

The piston 46 also has a cylindrical side wall 48 and a base portion 49. The base portion 49 is configured to define two opposed mounting lugs 51 and a web 53 extending between the lugs at the bottom end section of the piston 46. The web 53 may function as a bridge spanning the underside of the piston to strengthen to the piston.

In the arrangement shown, the piston 46 is at an uppermost condition within the passage 43 when adjacent the socket formation 33, and is movable towards and away from that uppermost condition. The piston 46 is shown in the uppermost condition in FIGS. 1, 2 and 7.

A power mechanism 61 is provided for moving the piston 46 towards the uppermost condition to effect movement of the syringe plunger 13 relative to the syringe barrel 12 to discharge fluid from the syringe through discharge outlet 14.

The actuator 45 comprising the piston 46 and the power mechanism 61, together provide a drive mechanism for moving the syringe plunger (13) relative to the syringe barrel (12) to discharge fluid from the syringe 11.

The power mechanism 61 comprises two spring mechanisms 63 disposed on opposed sides of the passage 43.

The spring mechanisms 63 are operably connected to the piston 46 to bias the piston into the uppermost condition. The spring mechanisms 63 are adapted to be progressively loaded upon movement of the piston 46 away from the uppermost condition, whereby the spring mechanisms exert a biasing force on the piston to urge it towards the uppermost condition.

In the arrangement shown, each spring mechanism 63 comprises a reel 64 and a flexible link 65 extending between the reel 64 and the piston 46. The flexible link 65 comprises a web or strip of flexible material 67 which can be wound onto and from the reel 64, with an inner end section (not shown) of the web or strip 67 attached to the reel 64 and an outer end section 69 attached to the piston 46. The outer end section 69 of the web or strip 67 is attached to a respective one of the lugs 51 provided at the bottom end section of the piston 46. In the arrangement shown, the outer end section 69 of each web or strip 67 is connected to the respective lug 51 by way of a fastener 71 such as a screw.

Each spring mechanism 63 further comprises a spring (not shown) adapted to be tensioned upon winding of the reel 64 in one direction, that being the direction corresponding to the web or strip 67 unwinding from the reel. In this embodiment, the spring comprises a spring capable of delivering a substantially uniform spring force when in a loaded condition; for example, a spring of known kind of the type commonly referred to as a watch spring. With this arrangement, the spring is tensioned upon movement of the piston 46 away from the socket formation 33, thereby loading the respective spring. The loaded spring can then be used to urge the piston 46 upwardly towards the socket formation 33, thereby causing the syringe plunger 13 to move relative to the syringe barrel 12 and dispense fluid from the syringe 11.

In the arrangement shown, each reel 64 is mounted on an axle 73 supported between the two housing sections 23, 24.

When the piston 46 is in a condition remote from the socket formation 33 defined by receptor 31, the length of the section of the passage 43 between the piston end face 47 and the socket formation 33 is at a maximum condition and of a size capable of accommodating the length of the syringe plunger 13 withdrawn from the syringe barrel 12 when the syringe 11 is in a fully loaded (full) condition. In other words, the passage 43 can accommodate the syringe plunger 13 withdrawn from the syringe barrel 12, with the formation 18 at the end of the syringe plunger 13 abutting the piston end face 47 and the syringe barrel 12 mounted onto the syringe pump 10 by way of the bayonet connection 37.

Figure 9:
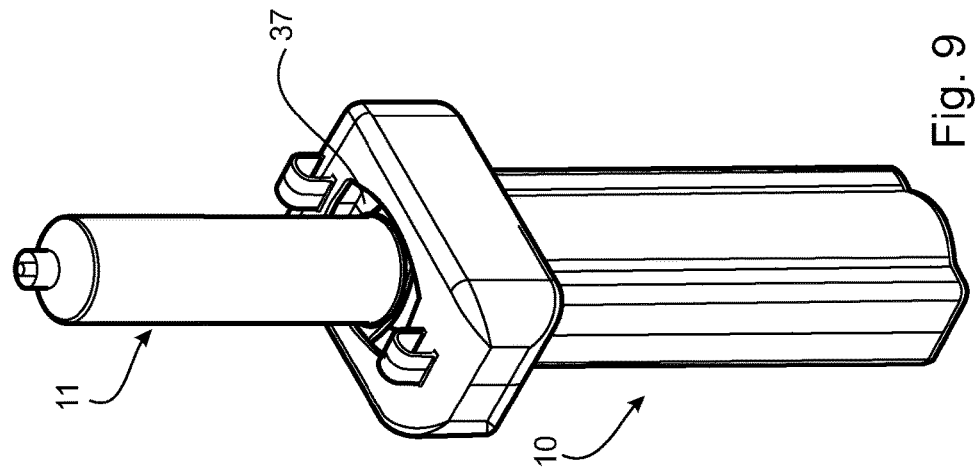
FIG. 9 is a view similar to FIG. 7, but showing the syringe being installed in position on the syringe pump.
Figure 8:
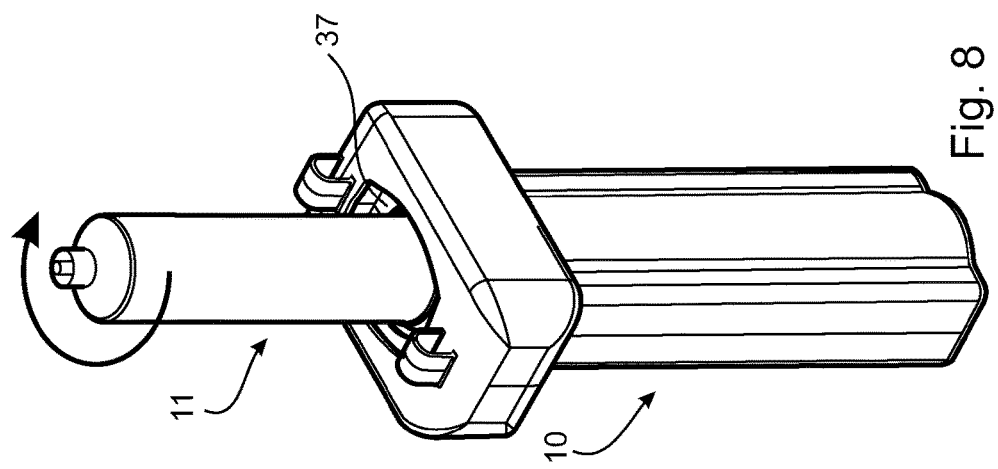
FIG. 8 is a view similar to FIG. 7, but showing the syringe being installed on the syringe pump.

In operation, the syringe 11 is filled to the extent desired and then arranged to prevent fluid discharging through the discharge outlet 14. This may be done in any appropriate way; for example, by fitting a closure to the discharge outlet 14 or by installing a delivery line on the discharge outlet 14 with a valve, clamp or other flow restrictor provided to prevent flow along the delivery line. With the discharge outlet 14 so blocked and the syringe plunger 13 in an extended condition, the syringe 11 is installed on the syringe pump 10. At this stage, the piston 46 is in the uppermost condition adjacent the socket formation 33 of the receptor 31. The syringe 11 is presented to the syringe pump 10 in the manner shown in FIG. 7, with the rear end section of the syringe plunger 13 leading. The extended syringe plunger 13 is inserted into the socket formation 33, with the formation 18 on the rear end section of the syringe plunger 13 engaging the piston end face 47. The syringe 11 is then pushed against the spring-biased piston 46, causing the piston to progressively move along the passage 43 away from the uppermost condition adjacent the socket formation 33. At this stage, the reaction force imposed upon the syringe plunger 13 cannot cause the syringe plunger to move relative to the syringe barrel 12 because the fluid contents of the syringe 11 are precluded from being expelled through the discharge outlet 14 because the latter is blocked against fluid flow. The syringe 11 is pushed towards the syringe pump 10 until such time as the lateral protrusion 15 on the rear end section 12a of the syringe barrel 12 is received in the entry end 38 of the socket formation 33 (with, of course, the syringe 11 being appropriately oriented such that the two opposed lugs 16 are in registration with the end sections 39a of the entry end 38). The syringe 11 is then rotated, as is depicted in FIG. 8, to engage the two opposed lugs 16 with the slots 35 in the socket formation 33, thereby completing the bayonet connection 37. This couples the syringe 11 to the syringe pump 10 and secured the syringe barrel 12 against movement. At this stage, the syringe 11 is installed on the syringe pump 10 and ready for use, as shown in FIG. 9. In the installation process, the piston 46 has been displaced along the passage 43 away from the uppermost condition, thereby loading the spring mechanisms 63. The piston 46 cannot move under the influence of the spring mechanisms 63 until such time as the discharge outlet 14 of the syringe 11 is unblocked to allow fluid to be expelled from the syringe. Once the discharge outlet 14 of the syringed is unblocked, the biasing force exerted on the piston 46 by the spring mechanisms 63 causes the piston to be progressively moved towards the uppermost condition in a controlled fashion, thereby operating the syringe 11 to deliver fluid at a controlled rate.

Figure 11:
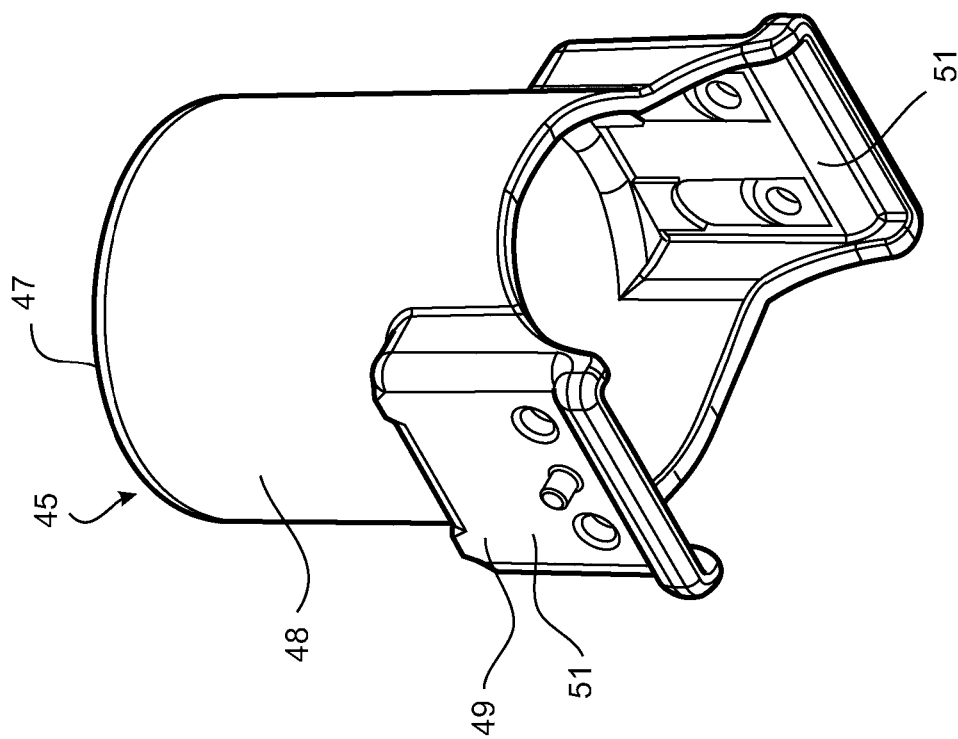
FIG. 11 is a perspective view of the actuator shown in FIG. 10.
Figure 10:
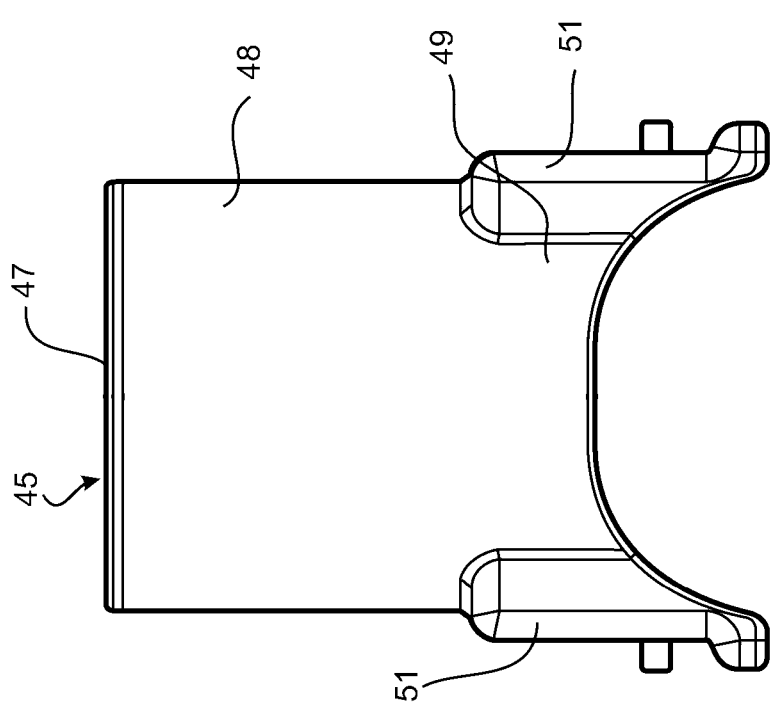
FIG. 10 is a side view of an actuator forming part of a second embodiment of a syringe pump according to the invention.

Referring to FIGS. 10 and 11, there is shown an actuator forming part of a second embodiment of a syringe pump according to the invention. The second embodiment of the syringe pump is similar in many respected to the first embodiment and similar reference numerals are used to denote similar parts. In this second embodiment, the piston 46 has a base portion 49 configured to define two opposed mounting lugs 51, but there is no web extending between the lugs at the bottom end section of the piston as is the case with the first embodiment.

The pump device 10 may provide a means to pump a fluid into a patient in a controlled manner. For example, the fluid may be a parenteral infusion of a drug or medicament. The pump device 10 does not require a motor; rather, it uses stored spring energy.

Accordingly, the pump device 10 may provide a syringe infusion device.

The syringe infusion device may allow for a constant safe pressure of fluid delivery. The syringe may be a 60 ml syringe, in which case the fluid may be delivered at a pressure of 13.5 psi.

With the syringe infusion device, it is possible to achieve commonly required flow rates for the administration of a fluid to a patient. For example, the charts in FIGS. 12 to 15 set out the parameters to determine the flow rate of a Flow Control Tubing (FCT) for an infusion volume of either 60 ml or 100 ml.

The substance contained within the syringe is preferably a fluid. The fluid may be any fluid, including water, saline, a drug suspension, therapeutic solution or suspension, antibiotics, chemotherapeutics, pain management drugs or other therapeutics substances known to a person skilled in the art. The fluid may comprise a fluid for therapeutic administration to a patient.

The syringe infusion device may constitute part of a syringe infusion system.

The syringe infusion system may be portable, allowing for infusion of a fluid over a short or prolonged period of time. For example, the syringe infusion system may be calibrated by a physician or nurse to infuse an amount of fluid over a pre-determined period of time. The period of time may be one hour or more depending on the nature of the fluid to be administered.

An advantage of the syringe infusion system is that there is no need to adjust any external switches. For example, when a syringe full of fluid is connected to flow tubing the syringe insertion into the pump bayonette fitting activates the pump with no need for external controls, such as a switch. This eliminates errors during operation.

Accordingly, and as discussed above, the present invention also provides an infusion system. The infusion system may comprise calibrated tubing with or without the use of a pump device (such as a syringe pump 10). Where there is a pump device, the latter preferably comprises a pump device according to the present invention, such as for example a syringe pump 10. However, the infusion system need not necessarily feature a syringe driving means in the form of syringe pump 10; it may feature any other appropriate form of syringe driving means.

One infusion system of the present invention comprises a syringe driving means that maintains a constant pressure within a syringe (for example a pressure of 500 mmHg in a 60 ml syringe or 300 mmHg pressure in a 100 ml syringe (+−20% mmHg)) and tubing with viscosity corrections for various antibiotic concentrations. The tubing is calibrated to restrict the flow of fluid thereby delivering the ideal profile of antibiotic to maximise the concentration of antibiotic above the mean inhibitory concentration (MIC) of the antibiotic to a patient in need thereof. The desirable flow rate also protects the integrity of the veins. The infusion system of the present invention may be used in the hospital setting or in the home environment for peripheral line, peripheral inserted central catheter (PICC) or central line antibiotic delivery.

When used for peripheral line infusions, a delivery over one hour with a reusable line (tubing) incorporating a swabable valve and air removing filter allows for up to 11 separate one hour infusions utilizing separate syringes containing a 60 ml dose each. Each of the syringes containing its dose may be attached to the same tubing and with appropriate spacing between each infusion. For example, it is possible to delivery three separate infusions of the antibiotic cephalosporin and eight separate infusions of an antibiotic such as fluocloxacillin. This allows for the use of a dilute solution for each separate dose and thus maintaining a high antibiotic serum level, with a maximum interval of eight hours with the three doses of cephalosporin's and a maximum interval of two hours between the substance being delivered over eight infusions per day.

For the Central Line and V set modified peripheral inserted central catheter (PICC) lines minimal time, and no contact between antibiotic mixtures occurs with a 13 hour delivery system delivering all of the antibiotic within the 24 hour period even when up to 8 g of powered antibiotic was delivered in a 24 hour period. When less than 3 g of powered antibiotic was delivered over a 24 hour period a 19 hour set corrected the flow to insure this was delivered over the 24 hour period. The critical V set modification to the PICC lines insured each antibiotic reached the end of the end of the leur lock fitting connected to a peripheral line or a PICC line if two antibiotics were being delivered at the same time so as to guarantee no contact time until the entered the PICC line or IV cannula sitting in the patients vein.

FIGS. 12 to 15 set out the information required for calibrating the tubing, based on the predetermined infusion time and rate. The tubing is referred to as Flow Control Tubing (FCT). FIGS. 12 to 14 provide information for the flow rate of an infusion volume of 60 ml. FIG. 15 provides information on FCT for an infusion volume of 100 ml. From these tables it is possible to calculate the required diameter and length of tubing to administer a 60 ml or 100 ml volume of antibiotic to a patient, depending on the viscosity of the antibiotic solution.

A new packaging system is described which allows antibiotics and other drugs packed in ampoules or bottles to be delivered with tubing that connects the drug when placed in a standard commercially available syringe through tubing that is corrected for viscosity to insure accurate delivery of the drug every time using a syringe drive mechanism that is reusable and also allows that new syringe drive mechanism in other applications described herein.

The invention further provides a new antibiotic or other drug packaging system whereby a powered or non powered drug is supplied in a container (bag or box) with a length of tubing measuring 1 cm to 300 cm in length, where the tubing is calibrated to automatically deliver the contents of the ampoule that is supplied in the same packaging at the manufacturer's prescribed rate with the flow resistance in the tubing adjusted to the viscosity for a 60 or 100 ml (or other) syringe that attaches through a bayonet fitting, to a pump device operable with a syringe, having a barrel and a plunger, the syringe pump being operable to cause relative movement between the syringe and the plunger and the syringe barrel for discharging fluid from the syringe, the syringe pump comprising a portion adapted to engage the syringe barrel to discharge fluid from the syringe, the drive mechanism comprising an actuator adapted to engage the plunger and a power mechanism for moving the actuator adapted to engage the plunger and a power mechanism for moving the actuator through the action of two compression force springs or watch springs producing parallel forces moving the actuator to effect movement of the syringe plunger relative to the barrel and so allow just the addition of a length of tubing to deliver the software (viscosity and resistance adjusted tubing) to automatically deliver the drug in exactly the right time when connected to a standard commercially syringe supplied off the shelf.

In another embodiment of the invention, there is provided a reusable tubing set with a valve that can be swabbed to remove bacteria, that is permanently attached at the end of tubing designed to control the flow rate of antibiotic and along the line an air removing filter protects the patient from clumsy operators who might accidently add air to the line with a result that a single tube can control the rate of drug delivery for a syringe attached to the drive mechanism described above and that tube may be attached and reattached to a series of syringes over a 72 hour period or longer.

Furthermore, the present invention provides an infusion system where two separate lines targeting delivery of water from a syringe over 13 hours (+−30%) and a line designed to deliver over 18-19 hours (+−30%) allows delivery of 3 g or less of powered antibiotic in less than 24 hours through the 18-19 hour tubing and 3-10 grams of antibiotic delivered through the 18-19 hour tubing in less than 24 hours with an infusion system comprising a syringe driving means that maintains a constant pressure through the parallel compression force springs or watch springs within the syringe with resistance and visit adjustment to control desired delivery rate.

In another embodiment of the present invention there is provided a reusable tubing with a delivery rate of 5-200 minutes for an antibiotic or a drug. Delivery may be selected as a practical reusable set that includes the swabable valve and air removing filter allowing a series of antibiotics that may be different to be delivered through the same line and using the same drive mechanism. In addition, multiple filled syringes may be used that have been prefilled and sent to the ward or home.

In one embodiment of the invention, the infusion lines may be adapted to provide patient controlled analgesia with or without a background infusion where a segment of resistance tubing controls the rate of filling of a patient controlled dose cavity, which has a high pressure activated valve down line to the patient dose cavity and may have a segment of tubing that is proximal to the patient dose cavity and connected beyond the high pressure valve so that patient activation causes a flush beyond the high pressure valve and the segment allowing flow past the valve allows a continuous flow of analgesia as a background infusion when included in the system.

In one further embodiment of the present invention there is provided an adaptation of the system to provide a single line or series of lines which may be connected to a female leur lock adaptor so that each line controlled the flow of viscous or non-viscous fluids designed to give subcutaneous delivery of a potentially irritant subcutaneous drugs to multiple sites, where the resistance to flow was built or designed into each separate tubing segment.

EXAMPLES

Example 1

Administration of a Therapeutic Agent Using a Pump Device

The following example describes the administration of an antibiotic solution to a patient in need thereof using the pump device of the present invention. The antibiotic is administered in a total volume of 60 ml, using a 60 ml syringe. In one example, the syringe is purchased from B Baun and Becton Dickinson (BD). When a 100 ml syringe is used, the syringe is supplied from JMS.

The antibiotic solution to be delivered to the patient is prepared using methods known in the art. In this example, the antibiotic is in powdered form and is made up to the required volume in accordance with the manufacturer's instructions. For example, 3 g of cephalosporin was made up in 60 ml of water.

A 60 ml syringe was attached to the vessel containing the antibiotic solution and loaded by withdrawing the plunger of the syringe from within the syringe barrel in order to fill the syringe with the solution. Once the total volume of the antibiotic solution is loaded into the barrel, the syringe can then be connected to the cannula or suitable tubing system designed to administer the antibiotic to the patient. It is important that the free end of the tubing (i.e. the end of the tubing not connected to the syringe) is closed to maintain the pressure within the syringe barrel. In this example, the pressure to be achieved within the syringe is 500 mm/Hg once attached to the pump device.

The syringe is then held orientating the outlet end facing upwards. The plunger flange is placed within the receiving portion of the body of the pump device. Preferably, the pump device is placed on a solid flat surface. Alternatively, the pump device may be secured in a stand that has been designed to assist with placing the syringe into the pump device.

Once the pump device is stable on a flat solid surface and the syringe, with the plunger end positioned on the top face of the piston (i.e. the receiving portion of the body of the pump device), the syringe is forced downwards against the top of the piston. Pressure by hand is applied to force the piston into the body of the device so that the syringe flange can be twisted into the bayonet receiving portion, locking the barrel and therefore the syringe in place. The syringe plunger is forced into the body of the pump device, forcing the piston downwards towards the distal end of the pump device.

As the piston moves downwards into the chamber of the pump device, the compression force springs positioned on either side of the piston stretch and the piston moves downwards. The syringe is now positioned within the pump device ready for use.

The tubing attached to the syringe outlet 14 is then attached to a cannula or other appropriate system already in place on the patient's vein. For example, the tubing or cannula that is attached to the patient is swabbed with alcohol, the cap on place on the tubing attached to the syringe is removed and the syringe is quickly attached to the patient. Once the cap is removed from the end of the tubing secured to the syringe, the pumping device immediately forces the fluid from the syringe barrel. As mentioned, the fluid will flow at a pressure of 500 mm/Hg. It is possible to further control the flow rate of the fluid from the syringe by adjusting the length and diameter of the tubing.

Once the syringe pump 10 commences the controlled flow of the solution from the syringe 11, it is possible for the syringe pump to be carried around. In one example, the syringe pump has a number of hooks (such as attachment points 27) on the exterior surface for attaching a lanyard so that the syringe pump can be hung around the patient's neck or hung on a stand. In another example, the syringe pump can be placed in a bag or even in the hood on the back of the patient's jacket. Thus, the pump device is portable.

At the end of the infusion, the patient or nursing staff can remove the syringe together with the syringe pump. If further drugs are required to be administered, the above process can be repeated.

Example 2

Single Use Infusion Tubing

Over 50 different antibiotic drugs were investigated and it was found that the common dosage is either 1 to 3 g per day in a 60 ml volume or 3 to 8 g per day in a similar volume. As the amount of antibiotic in the solution increases, so does the viscosity of the solution. It has been discovered that these doses can be accurately administered to a patient without the need for expensive pump systems or by nursing staff by the use of tubing calibrated to take into account the flow rate and duration of time for administering the antibiotic solution.

In this example, the patient to be treated requires a dose of antibiotics to be administered in accordance with the manufacturer's instructions and/or a general practitioner's instructions. For example, the patient is administered 1 g of cephalosporin in a total volume of 60 ml. The manufacturer's instructions will indicate the required volume, amount of antibiotic and the length of time that the antibiotic is administered.

Presently, this is achieved by the nursing staff reviewing manufacturer's tables for each product and entering the required information into an electronic pump to pre-set the correct conditions for flow rate and volume. The antibiotic is made up to the required volume and then the vessel containing the antibiotic solution is placed into the electronic device, the information for flow rate, and duration of dose time is entered. This is often time consuming and has an error associated with the data entry process (human error).

In this example of the present invention, there is no requirement for tables of information or an electronic pump that requires calibrating. Rather, the antibiotic is made up in solution and the vessel containing the antibiotic solution is attached to the end of a pre-calibrated tubing.

The tubing has been calibrated to take into account the viscosity of the antibiotic solution and the desired time for administration. The appropriate tubing is packed with the antibiotic to be administered.

In this example, the antibiotic is 1 g of cephalosporin to be made up to 60 ml with a suitable solvent. The viscosity of this solution is measured and the tubing calibrated to a length and diameter that will administer the total dose of the antibiotic in 1 hour.

Thus, in this example, the kit comprises an ampoule of 1 g of cephalosporin and a calibrated tube of length and diameter to administer 1 g of cephalosporin in 1 hour in accordance with the manufacturer's instructions.

The single use tubing may be used in combination with a pump device of the present invention, which allows for a pressure of 500 mmHg. Alternatively, the tubing can be used with another suitable pump known in the art.

Example 3

Peripheral Line Infusions for Up to 3 to 4 Hours

In this example, the infusion system comprises a length of tubing that has been calibrated to administer 3 g of an antibiotic in 3 hours. The tubing has a proximal end and a distal end. One end of the tubing (proximal end) has a valve, which can be swabbed in order to reduce the risk of infection. Along the tubing an air filter may be positioned, if necessary. The air filter compensates for any air that has been accidentally introduced into the tubing during loading of the antibiotic into the tubing. The distal end of the tubing is then connected to the patient.

The proximal end of the tubing may be connected to a vessel containing the antibiotic solution. The valve is in the closed position, preventing flow of the solution along the tubing. Once the valve is opened, the solution will flow along the tubing which has been calibrated (via the length of tubing and the diameter) to allow the solution to flow into the patient at a pre-determined flow rate.

Example 4

Peripheral Line Infusions for Up to 24 Hours

One disadvantage of commonly used methods for administering antibiotics via intravenous infusion is the inability to maintain a minimum inhibitory concentration (MIC) of the antibiotic in the patient's blood. That is, the antibiotic solution is infused over short periods of time, resulting in peaks and lows of the antibiotic in the blood. The present invention aims at increasing the MIC to ensure that a constant level of antibiotic is maintained in the blood system. For example, the tubing can be calibrated to ensure that the antibiotic is administered over a prolonged period of time.

For volumes of 60 ml or 100 ml the antibiotic solution should be administered at pressures less than 500 mm/Hg and preferably 300 mm/Hg, in order to maintain the integrity of the vein receiving the infusion. This is the first time that it has been possible to administer a volume of 60 ml or 100 ml via a tubing and portal pump that is not electronically controlled.

Thus, the calibrated tubing and the pump device of the present invention are used in combination to provide a pre-determined and constant flow rate of antibiotic to the patient over a pre-determined period of time.

It is also possible to use the tubing in combination with a V set.

Example 5

Currently there are no PCA pump systems on the market which involve a set with no reservoir cavity and no aspiration or driving system as part of the set. The sets as described below aim to achieve a low cost product for PCA sets. The version descried below comprising the spring in the patient dose bolus cavity could function with their 60 ml syringe attached where no pump device of the present invention, or other pump device. It is recommended that a reusable security box to be used with these PCA devices is also supplied to enhance safe use.

In the QA assurance of the set, the patient would be asked to attach the set to the 60 ml pump device of the present invention, and then confirm at five (5) minutes after the bolus dose cavity fills that no fluid travelled beyond the high pressure valve. This instruction involves the user in the quality assurance of the most critical safety element in the system at the time of priming their system. This principal of involving the pharmacist or doctor or nurse in checking the safety of the system also adds a unique method of risk control.

The following provides examples of further tubing sets that are specific to the 60 and 100 ml the pump device of the present invention.

Although there are four sets which the following examples describe, these sets use the 60 ml the pump device of the present invention: as an example.

Intravenous PCA set for 0.5 ml bolus dose with a 5 minute fill time and no background infusion.

The set contains a female leur lock fitting which attaches to the outlet of the 60 ml BD syringe (or other approved brands). The female leur lock fitting connects with a segment of tubing calibrated to control the flow of fluid, wherein the tubing is calibrated to deliver a volume of 0.5 mls in 5 minutes. In this example the tubing is 40 cm in length.

In this example a one way valve that opens at a low pressure (below 500 mmHg) controls the fluid flow to the next segment. This segment is connected to a Y or T shaped limb where one of the limbs fills a 0.5 ml cavity that can easily be pressed on after it fills and the other connects to a spring loaded valve with an opening pressure as high as 2000 mmHg. (This valve preferably has an opening pressure significantly above the pressure generated by the pump device of the present invention).

Because of the high opening pressure no flow beyond the valve will occur unless pressure is applied to the 0.5 ml cavity. The cavity must be constructed of a material that limits the filling to a fixed volume such as 0.5 mls and allows pressure applied to the cavity to easily generate a pressure above the 2000 mmHg pressure to open the high pressure valve that stops the flow of the fluid (the cavity may be shaped as a balloon shape or a syringe shape where the syringe fills to 0.5 ml only).

The fluid flows beyond the high pressure valve in this example to the patient over a typical length of 60 cm and preferably but not necessarily goes through an air removing filter. The final component in this system is a male leur lock that connects to the patients IV fittings.

This product then fills a 0.5 ml cavity over a 5 minute period and has no flow unless the cavity is pressed by the patient with a pressure great enough to open the high pressure spring controlled valve. In this way the world's first PCA system that involves just a length of tubing with valves and a cavity that can be pressed on becomes the world's most cost effective patient controlled analgesia systems. The tubing system can be used with standard 60 ml syringe and the 60 ml the pump device of the present invention available in hospital wards and will allow these low cost PCA's to be used.

Example 6

With the PCA version that requires a background infusion rate, a limb that is above the bolus dose cavity bypasses the high pressure vale so that the set always gives a constant flow such as 1 ml per hour. This set would therefore give a background infusion of 1 ml per hour but with 12 presses per hour could deliver a maximum of a total of 7 mls per hour.

Example 7

Epidural PCA Version of the Pump

In the epidural version of the pump a continuous background infusion of 5 mls an hour could easily be delivered with the same design. For the epidural bolus version a typical filling of 4 ml would occur over 15 minutes.

Example 8

Tubing Sets for Infusion Systems

The following tubing systems may be used in conjunction with the pump device of the present invention.

This set contains a female leur lock fitting which attaches to the 60 ml BD syringe (or other approved brands). The female leur lock fitting connects with a segment of tubing which controls the flow of fluid to a volume of 0.5 mls in 5 minutes and for this example, the tubing is 40 cm in length. In this example, a one way valve that opens at a low pressure (below 500 mmHg) controls the fluid flow to the next segment. This segment is connected to a Y or T shaped limb where one of the limbs fills a 0.5 ml cavity that can easily be pressed on after it fills and the other connects to a spring loaded valve with an opening pressure as high as 2000 mm Hg. Preferably, the valve has an opening pressure significantly above the pressure generated by the a pump device, such as the pump device of the present invention.

Because of the high opening pressure no flow beyond the valve will occur unless pressure is applied to the 0.5 ml cavity. The cavity must be constructed of a material that limits the filling to a fixed volume such as 0.5 mls and allows pressure applied to the cavity to easily generate a pressure above the 2000 mmHg pressure to open the high pressure valve that stops the fluid flow. For example, the cavity may be shaped as a balloon shape or a syringe shape where the syringe fills to 0.5 ml only).

In this example, the fluid flows beyond the high pressure valve into the patient over a typical length of tubing of 60 cm and preferably (but not necessarily) goes through an air removing filter. The final component in this system is a male leur lock that connects to the patients IV fittings.

This product then fills a 0.5 ml cavity over a 5 minute period and has no flow unless the cavity is pressed by the patient with a pressure great enough to open the high pressure spring controlled valve. In this way this is the first PCA system that involves just a length of tubing with valves and a cavity that can be pressed on becomes a more cost effective patient controlled analgesia systems. The standard 60 ml syringe and a 60 ml pump device will be available in hospital wards and will allow these low cost PCA's to be used.

In a second example of the PCA version where there is needed a background infusion rate, a limb that is above the bolus dose cavity bypasses the high pressure valve so that the set always gives a constant flow such as 1 ml per hour. This set would therefore give a background infusion of 1 ml per hour but with 12 presses per hour could deliver a maximum of a total of 7 mls per hour.

In a further example, the epidural version of the pump device delivers a continuous background infusion of 5 mls an hour, easily delivering with the same design as described above. For the epidural bolus version a typical filling of 4 ml would be possible over 15 minutes.

A kit is provided that contains a syringe, tubing and the syringe infusion device. A syringe (60 or 100 ml) is filled with the required fluid. For example, the fluid is a solution of naltrexone in saline. The plunger of the syringe is pushed into the barrel of the syringe to remove all air from the syringe, as in normal practice. The appropriate tubing is attached to the end of the syringe as is known in the art. The distal end of the tube is then attached to the appropriate cannula or other suitable device.

The syringe is then placed into the syringe infusion device so that the syringe is resting in the depression on the interior surface of the syringe mounting portion. Pressure is forced onto the plunger to ensure the syringe is primed ready to go.

Once infusion of the fluid is completed, the syringe may be removed from the syringe infusion device.

The invention claimed is:

1. A pump device operable with a syringe having a barrel and a plunger, the pump device being operable to cause relative movement between the syringe plunger and the syringe barrel for discharging fluid from the syringe, the pump device comprising a portion adapted to engage the syringe barrel, and a drive mechanism for moving the syringe plunger relative to the barrel to discharge fluid from the syringe, the drive mechanism comprising (1) a piston adapted for guided movement along a path, configured to stay outside the barrel during the relative movement between the plunger and the barrel and having a cylindrical side wall, and (2) a power mechanism for moving the piston to effect movement of the syringe plunger relative to the barrel, wherein the power mechanism comprises two spring mechanisms operable to exert a spring force on the piston, wherein each spring mechanism comprises a reel and a flexible link, the flexible link having a proximal end attached to the reel and a distal end directly attached to the piston, wherein the flexible link is windable onto and from the reel, wherein each reel is mounted on an axle supported between two housing sections of the pump device; and wherein the piston comprises a base portion and an upper end face, the base portion is configured to define two opposing mounting lugs each directly attached to one distal end of one flexible link and a web functioning as a bridge extending between the lugs and the upper end face of the piston is adapted to directly engage the plunger.

2. The pump device according to claim 1, wherein the power mechanism has a first condition which it assumes when not in operation and a second condition from which it is operable to move the syringe plunger relative to the barrel.

3. The pump device according to claim 2, wherein the power mechanism is adapted to be energising upon movement from the first condition to the second condition.

4. The pump device according to claim 2, wherein the power mechanism is movable from the first condition to the second condition upon installation of the syringe on the syringe pump.

5. The pump device according to claim 1, wherein the two spring mechanisms are disposed on opposed sides of the path along which the piston is movable.

6. The pump device according to claim 1, wherein said portion adapted to engage the syringe barrel comprises an engaging means for releasably engaging an end section of the barrel from which the plunger extends.

7. The pump device according to claim 6, wherein the engaging means comprises a receptor in which the end section of the barrel is releasably receivable.

8. The pump device according to claim 7, wherein the receptor is configured as a socket formation for operation in conjunction with the end section of the barrel to provide a connection therebetween.

9. The pump device according to claim 8, wherein the socket formation is configured to provide a bayonet connection.

10. The pump device according to claim 9, wherein the receptor is configured to define two bayonet slots adapted for engagement with two bayonet pins on the syringe barrel, the bayonet pins comprising opposed lugs against which a user can locate fingers of a hand in which the syringe is being held to restrain the syringe barrel while pushing the syringe plunger with the thumb of the hand.

11. The pump device according to claim 1, further comprising a cavity formed by the two housing sections in which the piston is accommodated, the cavity defining the path along which the piston is movable, a receptor being provided adjacent one end of the cavity whereby the syringe plunger is receivable in the cavity for engagement with the piston.

12. The pump device according to claim 11, wherein the cavity comprises a passage configured to define a barrel portion along which the piston is guidingly movable.

13. The pump device according to claim 1, wherein each distal end of each flexible link is directly attached to the piston with a screw.

* * * * *